United States Patent [19]
Sabourin et al.

[11] Patent Number: 6,082,198
[45] Date of Patent: Jul. 4, 2000

[54] METHOD OF ULTRASONICALLY INSPECTING TURBINE BLADE ATTACHMENTS

[75] Inventors: Paul F. Sabourin; Gregory P. Selby, both of Charlotte, N.C.

[73] Assignee: Electric Power Research Institute Inc., Palo Alto, Calif.

[21] Appl. No.: 09/223,693

[22] Filed: Dec. 30, 1998

[51] Int. Cl.[7] .................................................. G01N 29/00
[52] U.S. Cl. ................................................. 73/633; 73/628
[58] Field of Search ............................. 73/618, 620, 621, 73/625, 626, 627, 628, 632, 633

[56] References Cited

U.S. PATENT DOCUMENTS

| | | | |
|---|---|---|---|
| 3,918,295 | 11/1975 | Herbertz | 73/67.7 |
| 4,052,889 | 10/1977 | Mucciardi et al. | 73/602 |
| 4,241,608 | 12/1980 | Dees et al. | 73/606 |
| 4,354,388 | 10/1982 | Diepers et al. | 73/612 |
| 4,441,369 | 4/1984 | Lessard et al. | 73/602 |
| 4,497,210 | 2/1985 | Uchida et al. | 73/602 |
| 4,624,143 | 11/1986 | Green | 73/620 |
| 4,966,746 | 10/1990 | Richardson et al. | 376/249 |
| 5,009,105 | 4/1991 | Richardson et al. | 73/621 |
| 5,111,696 | 5/1992 | Lund et al. | 73/627 |
| 5,408,884 | 4/1995 | Sabourin | 73/649 |
| 5,423,220 | 6/1995 | Finsterwald et al. | 73/642 |
| 5,460,180 | 10/1995 | Klepper et al. | 128/661.01 |
| 5,513,532 | 5/1996 | Beffy et al. | 73/628 |
| 5,541,468 | 7/1996 | Frey et al. | 310/334 |
| 5,544,655 | 8/1996 | Daigle | 128/661.01 |
| 5,546,946 | 8/1996 | Souquet | 128/662.03 |

FOREIGN PATENT DOCUMENTS 157302  10/1985  European Pat. Off. .

*Primary Examiner*—Richard A. Moller
*Attorney, Agent, or Firm*—Flehr Hihbach Test Albritton & Herbert LLP

[57] ABSTRACT

A method of simultaneously reconstructing and testing a straddle-mount turbine blade hub with the turbine blades in place. The method employs a sector scan ultrasonic phased array mounted on one face of the hub to inspect the opposite face.

8 Claims, 3 Drawing Sheets

METHOD OF ULTRASONICALLY INSPECTING TURBINE BLADE ATTACHMENTS

FIELD OF THE INVENTION

This invention relates generally to a method of ultrasonically inspecting turbine blade attachments and more particularly to a method of inspecting straddle-mount turbine blade attachments utilizing ultrasonic phased array techniques.

BACKGROUND OF THE INVENTION

Turbines are used for generating rotary mechanical power from the energy in a working fluid. The working fluid energy, originally in the form of pressure energy, is converted to velocity energy by passing through a system of blades in the turbine. Changes in the magnitude and direction of the velocity energy are made to cause tangential forces on the blades, producing mechanical rotation of a turbine rotor. The rotating turbine rotor may be positioned to interact with a generator rotor and generator stator and thereby produce electricity.

FIG. 1 is a simplified illustration of a rotor assembly 11 that includes a rotor shaft 12 supporting a number of blade assemblies 13, 14, 15, and 16. Each blade assembly includes a blade hub 17 that supports a number of blades.

Turbine rotors can be massive steel components sometimes weighing in excess of 200 tons. Steam turbines are used to convert thermal energy into usable work and are typically used to drive an A-C electric generator to produce electric power. The design of a turbine rotor permits most of the associated hardware to be integral to the rotor itself. The major exception is the blading that protrudes from the outside surfaces of the rotor forging. Blades are designed to take advantage of the steam conditions that change as the steam passes through the different stages of the turbine. The first blades encountered at the steam inlet are small in size but capable of withstanding high temperatures and pressures. As seen in FIG. 1, successive stages of the blades become larger to take advantage of the expanding steam as it cools. The blades are individually machined and assembled onto the rotors in groups.

The attachment of the blades to the rotor is accomplished by having machined surfaces on the blade and on the rotor that work together in a locking mechanism. The design of the blade attachment area varies among manufacturers and may vary from row to row on an individual rotor. In addition to the primary function of holding the blade to the rotor, the attachment area is designed to make it relatively easy to change the blades if they should be damaged during service. Even so, blade removal can be extremely time consuming. The process also has the potential for damaging the blades beyond repair. Consequently, blade removal is best avoided when possible.

There are several designs for the region where the turbine blades attach to the rotor. One of the more common attachment mechanisms is the straddle-mount design, FIG. 2. In this design, the hub 17 is carried on the rotor shaft 12. An arrangement of "hooks" 21 is machined around the entire periphery of the hub or "disk" in a fir tree configuration. The hub can either be an integral part of the rotor forging, machined to a disk shape, or a separate disk assembled to the central shaft. The blades include an attachment configuration that matches and engages the hooks 21 of the hub rim. At some location around the rim of the disk, the hooks are removed, i.e., machined away, for the width of one blade to provide a loading slot 22. Blades are loaded onto the disk rim by first mounting a blade over the rim at this loading slot and then moving it around the disk to engage the mating hooks. This is done sequentially, one blade at a time, until the entire periphery has been loaded. A special "closing" blade (not shown) is used in the loading slot. This blade is attached either by drilling and pinning it to the rim, by locking it to adjacent blades on either side of it, or by a combination of the two. The "hook" area of the attachment is under extremely high centrifugal stress when the rotor is rotating, making it susceptible to service-induced flaws or cracks 23. Although service-induced flaws are not restricted to the straddle-mount design, for the purposes of the disclosure, only the straddle-mount design is described.

Thermal and centrifugal stresses constantly act on the attachment areas when a turbine is in service. In certain areas where wet steam is present, possible aided by caustic steam conditions arising from less than adequate control of steam chemistry, and where stresses are adequate, service-induced flaws may initiate and grow by an intergranular stress corrosion cracking (IGSCC) mechanism in the attachment region. High temperature creep, mechanical fatigue, and combinations of the mechanisms may also cause cracking or aid the initiation and growth of stress corrosion cracking. Service-induced flaws on the blade side of the attachment occur occasionally. Generally, blade cracking occurs less frequently than disk cracking because less susceptible material can be used for the blades. In addition, blades tend to fail individually, resulting in limited damage. For service-induced flaws on the hub side of the attachment, however, initiation leading to propagation is not restricted to the region under only one blade. Left unchecked, cracking in the hub side of the attachment may, in certain designs, propagate under successive blades and groups of blades until catastrophic failure of the affected area occurs. Damage to the turbine and surrounding components outside the turbine may occur when large pieces of the rotor cannot be contained by the turbine shells.

Ultrasonic testing procedures are commonly used to examine turbine components for the purpose of detecting and characterizing service-induced flaws. The technique involves applying high frequency sound waves to a structure of interest. When the sound waves interact with an object that has a significant difference in acoustic impedance (the product of density and acoustic velocity) from that of the propagation medium, a portion of the sound is either reflected or diffracted back to the source from which the sound originated. Measurement and evaluation of the returned sound pattern permits determination of the presence and characteristics of the reflecting medium.

For ultrasonic techniques to work, it is necessary to discriminate between object architecture and flaws in the object architecture. This discrimination is readily accomplished when the object architecture is known. The test for service-induced flaws on the disk side of the blade attachment required knowledge of the attachment interlocking geometry. Several blade attachments are designed such that the surface geometry is visible from the side of the disk. However, the straddle-mount design is not visible from the side of the rotor.

Ideally, inspection of the hub blade attachment is best accomplished with the aid of machine drawings of the attachment region. Rotor manufacturers have machine drawings, but because of their proprietary nature, they are reluctant to provide them to outside sources for the purpose of inspection. Without the machine drawings, or knowledge of the attachment geometry, attempting to perform the geometry-dependent nondestructive evaluation is less than reliable.

Typically, the straddle-mount blade attachment region has been inspected by mocking up a scale drawing of its cross sectional area. The mockup will provide the specific transducer angles and locations necessary for the piezoelectric transducer to direct the sound at the points where service-induced flaws should initiate. This also provides the means to evaluate various reflectors to determine which are from the geometry of the blade attachments themselves, and which are from flaws emanating from the geometry. Essentially, this limitation reduces the effectiveness of anyone attempting to perform the inspection that had to rely on another method of determining the geometry without the blade attachment drawings. The process for performing the inspection then calls for the transducer to be placed on the side of the disk and, with the appropriate angle, aimed at the "hook" of interest on the opposite side of the disk. Scanning around the circumference of the hub is to be performed by using a fixture to place the transducer on the radial face disk and rotating the rotor while maintaining the relative transducer position dictated by the mockup drawing. Adjacent hooks are inspected by repositioning the transducer along the same radial face and again rotating the rotor. One scan is required for each hook to be inspected. Data obtained during the inspection can either be recorded manually or by the use of an automated system.

In U.S. Pat. No. 5,408,884 there is described a method for ultrasonic reconstruction of the turbine blade attachment structure. After the structure has been reconstructed, the inspection is then carried out as described above.

OBJECTS AND SUMMARY OF THE INVENTION

It is an object of the present invention to provide a method for ultrasonically inspecting straddle-mount turbine blade attachments without a prior knowledge of the straddle-mount configuration.

It is another object of the present invention to provide an ultrasonic inspection method which identifies and locates the attachment geometry and provides improved detection, sizing and characterization of service-induced flaws in straddle-mount configurations.

The foregoing and other objects of the invention are achieved by ultrasonically inspecting a straddle-mount hub with rotor blades in place by placing a phased array ultrasonic probe on one face of the hub and directing and sector scanning the opposite face to reconstruct and inspect the opposite face.

BRIEF DESCRIPTION OF THE DRAWINGS

The invention will be better understood from the following description when read in conjunction with the accompanying drawings as follows.

DESCRIPTION OF PREFERRED EMBODIMENT

Figure 1:
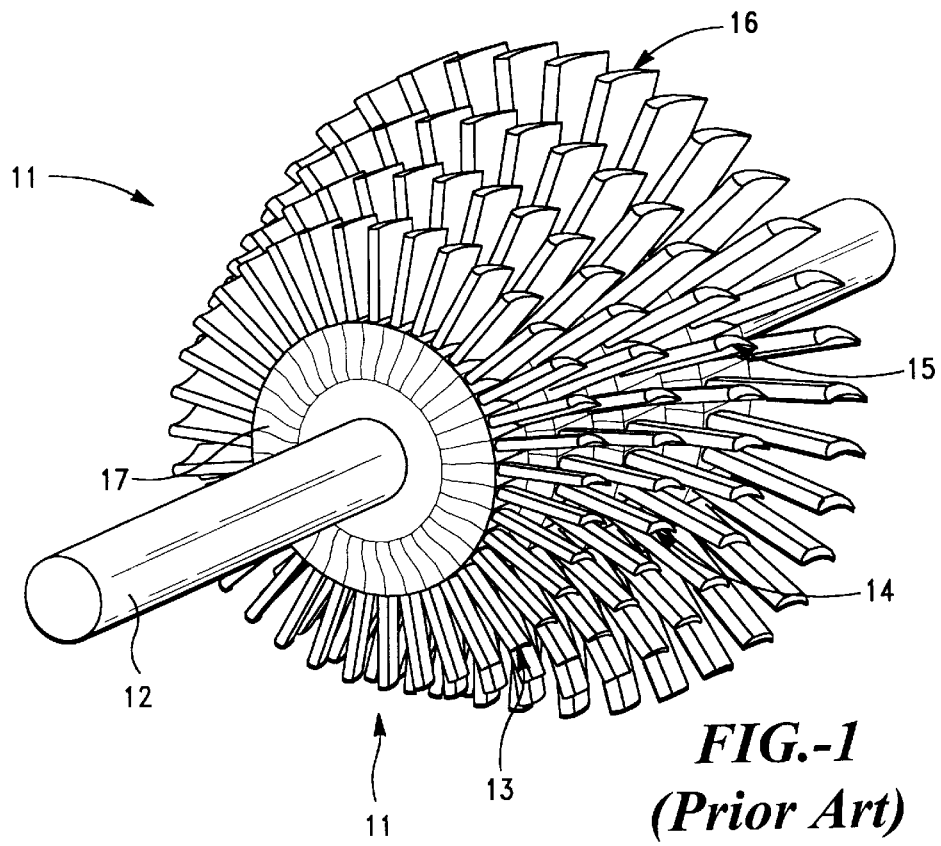
FIG. 1 is a schematic perspective view of a rotor assembly.
Figure 2:
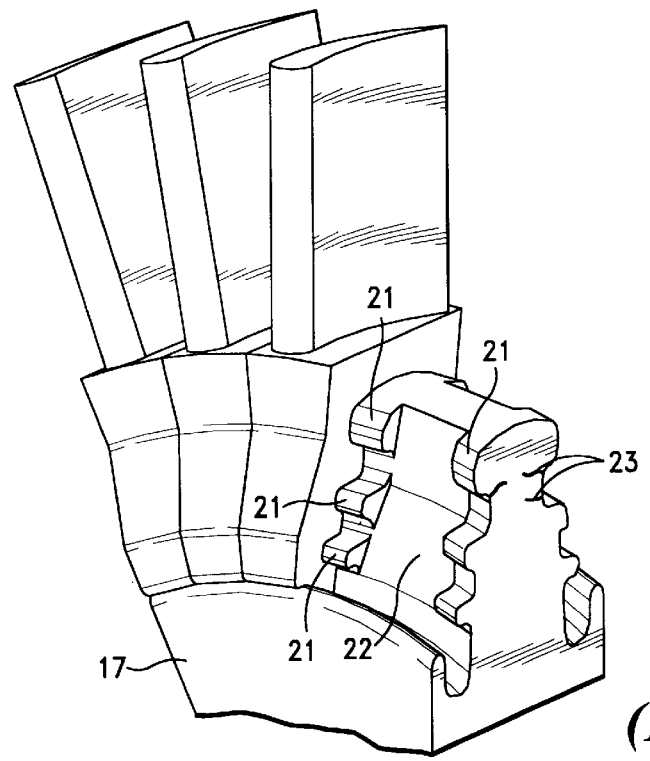
FIG. 2 is an enlarged perspective view of a straddle-mount rotor blade attachment hub with mounted rotor blades.
Figure 3:
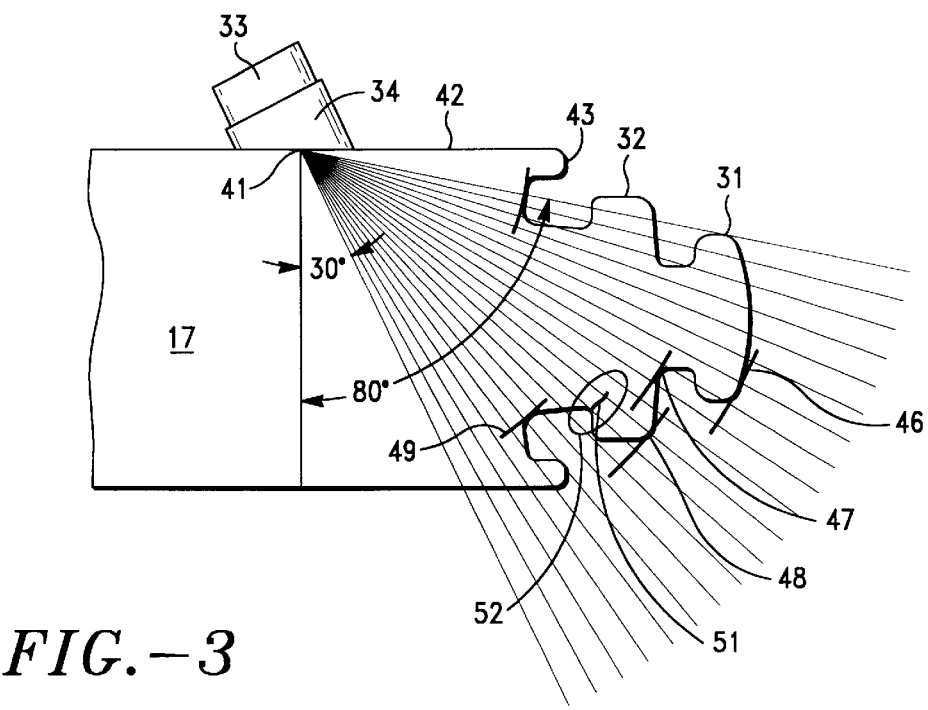
FIG. 3 is a cross-sectional view of a hub with a phased array ultrasonic probe mounted on one face and showing ultrasonic beams successively scanning the opposite face in a fan-shaped pattern.
Figure 4:
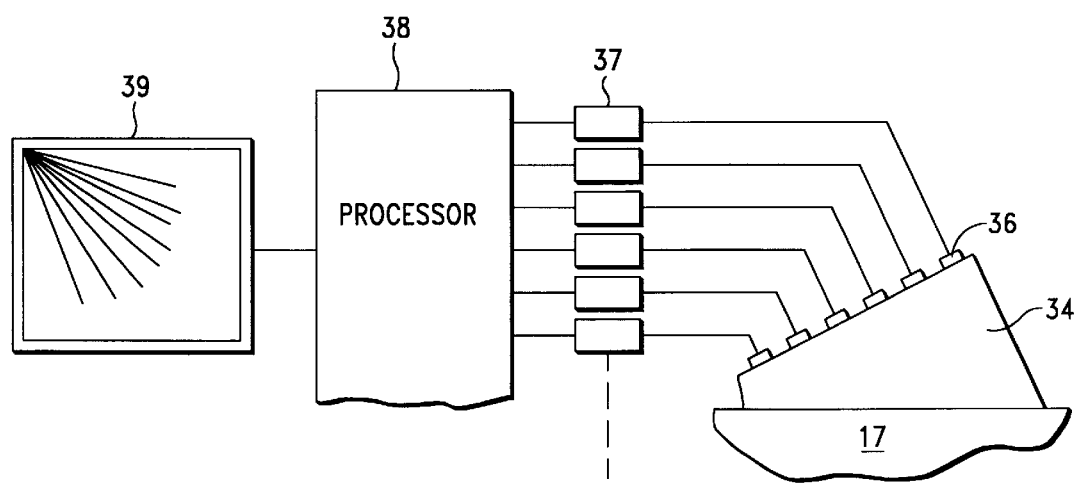
FIG. 4 is an enlarged view of the ultrasonic array schematically showing the pulser/receivers, processing circuits and display.

Referring to FIGS. 3 and 4, a two hook, 31,32, straddle-mount attachment region is sector scanned by a linear array ultrasonic probe 33 mounted on a wedge 34 which provides an interface between probe transducers and the hub 17. The linear array probe comprises a series of individual, small ultrasonic transducers 36 arranged in a row, FIG. 4. Each transducer element has its own electrical connections and is acoustically isolated from the other elements. Each element has its own pulser/receiver circuit 37 and produces its own radio-frequency time/amplitude response, called an "A-scan". The individual A-scans are summed by processor 38 and the resulting A-scan is saved and/or displayed on display 39. The angle, mode and focus of the ultrasonic beam are varied by controlling the timing of the pulse and reception for each element before the individual element responses are summed. When the array probe is programmed for the blade attachment application, the probe successively generates longitudinal-mode or shear-mode sound beams, or both, from (typically) 30 to 80 degrees, in one-degree increments, FIG. 3. Beam focusing may or may not be useful depending on the design of the array.

After the array probe has been calibrated for the correct beam exit point 41, and the ultrasonic system has been calibrated for the proper sound velocity, scanning may be performed. By sector scanning, the hub geometry reconstruction and inspection are accomplished simultaneously. The probe is placed on the face 42 of the hub such that the beam is directed radially outward and across the attachment toward the hooks 31, 32 on the opposite face of the hub. The relationship of the beam exit point to the tang 43 on same side of the hub is recorded for positional reference. The positions of two or more hooks may be recorded with either longitudinal or shear wave beam propagation when the probe performs its electronic fan-shaped sweep from 30 to 80 degrees.

FIG. 3 illustrates one slice taken through the hub 17. As the hub is scanned, the data processor system 38 records the echoes returned from the blade attachment hooks and flaws on the opposite side of the hub. In FIG. 3, echoes 46, 47, 48 and 49 are from the straddle-mount while echo S1 is from a crack 52. The data recorded for each azimuthal position will include the position of the probe related to the distance from the tang of the disk; the distance from the test surface on the radial face of the disk to each recorded reflector (hooks and flaws), and the beam angle at which each echo was detected.

The data acquisition and/or analysis software displays simultaneously the data recorded for all beam angles as a polar plot, creating a cross-sectional view called a "sector scan" image. The sector scan image includes the reflections received from the tang and all the hooks on the opposite surface of the disk, plus the end of the disk and the tang on the scanning surface of the disk. The positions of all these reflectors can be measured directly from the sector scan image. If a crack is present on the opposite surface of the attachment area anywhere between the tang and the end of the disk, its image will be displayed among the geometric reflectors. Its position and its depth can be measured directly from the image. If the crack is deep enough, it may "shadow" the normal reflection from one or more of the geometric reflectors. This effect can provide confirmation of detection and qualitative confirmation of depth measurements.

Figure 5:
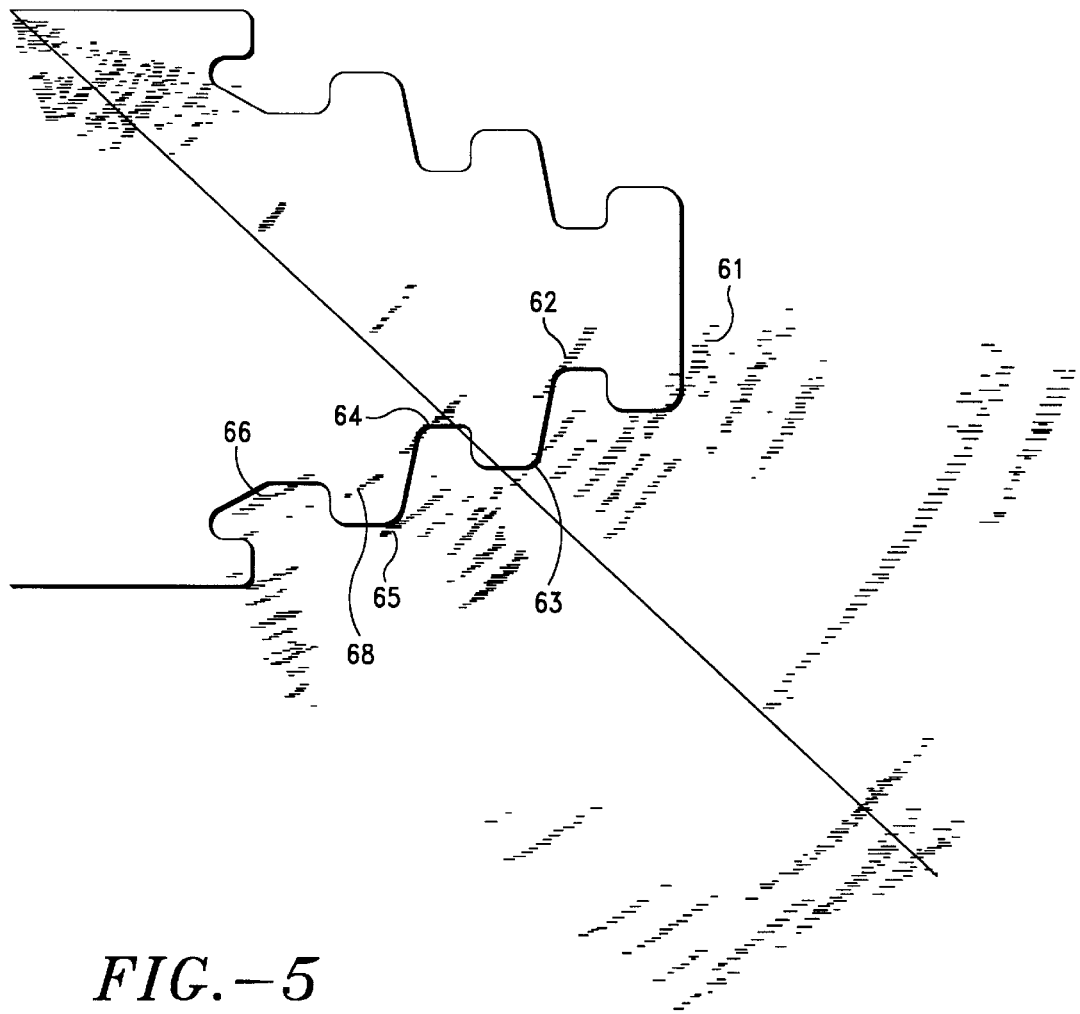
FIG. 5 shows an ultrasonic sector scan of a three-hook hub.

FIG. 5 shows an ultrasonic sector scan image of a three-hook attachment hub with hub attachment geometry overlaid. The scan was taken with a 10 MHz, 32 element array. The scan was from 20° to 70°, with longitudinal waves at 0.5° increments. The scan display shows echoes 61, 62, 63, 64, 65 and 66 from the straddle mount, and echo 68 from a crack in the power hook.

The benefit of the invention is in its accurate display of the positions of all tangs, hooks, and cracks simultaneously in correct geometric arrangement, with no foreknowledge of the shape, position, or even the number of attachments hooks. Conventional ultrasonic probes at a fixed radial position can only detect one adjacent pair of hooks, and monitor the space between them for cracking. They are incapable of mapping the entire cross-section because the beam angle is constant, and the width of the beam is limited. Inspection of the entire attachment area requires repeated scans using a single probe at several radial positions, or a single scan using one probe for each pair of hooks. In either case, accurate radial placement of the probe(s) is required to ensure that each probe detects two hooks simultaneously. Accurate placement is difficult because frequently the positions of the hooks are unknown. Radial drift of the probe's position due to scanner limitations can degrade the effectiveness of the inspection; such drift has no effect on the usefulness of data acquired using the array technique.

One skilled in the art will appreciate the importance of the present invention's ability to reconstruct and inspect a non-visible straddle-mount structure. The ability to ultrasonically test a rotor blade attachment structure with the blades in place saves time and money. The ability to simultaneously reconstruct and test the straddle-mount structure without the benefit of design drawings allows parties other than the manufacturer of the rotor assembly to test and maintain a rotor assembly.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. The method of ultrasonically testing a straddle-mount turbine hub of the type including hooks and tangs with rotor blades mounted on the hub comprising the steps of:

placing a phased array ultrasonic probe on one face of the hub with the rotor blades mounted on the hub, ultrasonically sector scanning a cross-section of the hub to simultaneously reconstruct the structure of the opposite face of the hub including the hooks and tangs and detect defects within the cross-section, and simultaneously indicating the position of the hooks and tangs and the position of defects within the cross-section relative to the position of the hooks and tangs.

2. The method of claim 1 in which the probe successively generates longitudinal-mode or shear-mode sound beams or both.

3. The method of claim 1 in which said probe includes a plurality of transducer elements, each including its own pulser/receiver circuit and the angle of the beam is controlled by controlling the timing of the pulses and reception by each transducer element.

4. The method of ultrasonically testing a straddle-mount turbine hub of the type including hooks and tangs with rotor blades mounted on the hub comprising the steps of:

placing a linear array ultrasonic probe on one face of said hub with the rotor blades mounted on said hub, exciting said linear array ultrasonic probe to generate successive sound beams which scan a cross-section of said hub in a fan-shaped pattern, said beams directed to the opposite face of said hub, receiving reflected sound at each of said beams simultaneously reconstructing the structure of the opposite face including the hooks and tangs and detecting defects within the cross-section, and simultaneously indicating the position of the hooks and tangs and the position of defects within the cross-section relative to the position of the hooks and tangs.

5. The method of claim 4 in which said probe includes a plurality of transducer elements, each including its own pulser/receiver circuit and the angle of the beam is controlled by controlling the timing of the pulse and reception of each transducer element.

6. The method of ultrasonically testing a straddle-mount turbine hub of the type including hooks and tangs with a plurality of rotor blades mounted on the hub comprising the steps of:

placing a linear array ultrasonic probe on one face of the hub with the rotor blades mounted on the hub, ultrasonically sector scanning a cross-section of the hub;

recording echoes returned from the hooks and tangs of the hub and from defects within the cross-section;

determining the beam angle at which the echo representing each hook and tang and each defect was recorded;

simultaneously displaying the data recorded for all beam angles creating a cross-sectional image indicating the relative positions of the hooks and tangs of the hub and the defects within the cross-section.

7. The method of claim 6 in which said determining step further includes determining the distance of the tang on the opposite face of the hub relative to the ultrasonic probe, the distance of each hook on the opposite face relative to the ultrasonic probe, and each defect within the cross-section relative to the ultrasonic probe.

8. The method of claim 6 in which said simultaneously displaying step further includes simultaneously displaying the data recorded for all beam angles as a polar plot creating the cross-sectional image.

* * * * *